US012736518B2

(12) United States Patent
Qin et al.

(10) Patent No.: US 12,736,518 B2
(45) Date of Patent: Sep. 15, 2026

(54) DEVICE AND METHOD FOR CALCULATING CHANGE IN $CO_2$ STORAGE CAPACITY BEFORE AND AFTER RESERVOIR DRYING

(71) Applicant: Southwest Petroleum University, Chengdu (CN)

(72) Inventors: Jiazheng Qin, Chengdu (CN); Ning Wang, Chengdu (CN); Yong Tang, Chengdu (CN); Youwei He, Chengdu (CN); Zhenhua Rui, Chengdu (CN); Yueliang Liu, Chengdu (CN); Maohan Yuan, Chengdu (CN)

(73) Assignee: Southwest Petroleum University, Chengdu (CN)

( * ) Notice: Subject to any disclaimer, the term of this patent is extended or adjusted under 35 U.S.C. 154(b) by 567 days.

(21) Appl. No.: 18/460,681

(22) Filed: Sep. 4, 2023

(65) Prior Publication Data

US 2025/0003945 A1 Jan. 2, 2025

(30) Foreign Application Priority Data

Jun. 30, 2023 (CN) ........................ 202310787606.3

(51) Int. Cl.
*G06F 11/30* (2006.01)
*G01N 33/24* (2006.01)

(52) U.S. Cl.
CPC .................................. *G01N 33/24* (2013.01)

(58) Field of Classification Search
CPC ..................................................... G01N 33/24
See application file for complete search history.

(56) References Cited

U.S. PATENT DOCUMENTS

2024/0319066 A1* 9/2024 He ........................ G01N 33/24

FOREIGN PATENT DOCUMENTS

| | | | |
|---|---|---|---|
| CN | 111155989 | * | 5/2020 |
| CN | 111155989 A | | 5/2020 |
| CN | 112986096 | * | 6/2021 |
| CN | 113075109 | * | 7/2021 |
| CN | 113075109 A | | 7/2021 |
| CN | 115034489 | * | 9/2022 |
| CN | 115034489 A | | 9/2022 |

* cited by examiner

*Primary Examiner* — Phuong Huynh
(74) *Attorney, Agent, or Firm* — Nitin Kaushik

(57) ABSTRACT

The present disclosure presents a device and method for calculating a change in $CO_2$ storage capacity before and after drying, wherein the method comprises the following steps: S1: acquire a target stratum core and prepare a formation water sample and a gaseous $CO_2$ sample; S2: measure the content of the saturated condensate water of the gaseous $CO_2$ sample under a target formation condition; S3: saturate formation water for the target stratum core; S4: perform displacement experiments until a water saturation of a core at the target stratum reaches saturation of irreducible water in an actual stratum, and record a core porosity $\phi_0$ at this time; S5: continue the displacement experiment until all the formation water in the core of the target stratum has evaporated, and record the core porosity $\phi_1$ at this time; S6: calculate a drying radius of reservoir and the change of $CO_2$ storage capacity after reservoir drying.

8 Claims, 3 Drawing Sheets

DEVICE AND METHOD FOR CALCULATING CHANGE IN $CO_2$ STORAGE CAPACITY BEFORE AND AFTER RESERVOIR DRYING

CROSS-REFERENCE TO RELATED APPLICATIONS

The application claims priority to Chinese patent application No. 2023107876063, filed on Jun. 30, 2023, the entire contents of which are incorporated herein by reference.

TECHNICAL FIELD

The present disclosure relates to the technical field of $CO_2$ geological sequestration, and in particular to a device and method for calculating a change in $CO_2$ storage capacity before and after reservoir drying.

BACKGROUND

With the society developing continuously, the energy consumption is also boosting, followed by the expanding consumption of fossil fuels such as coal, oil and natural gas, increasing carbon dioxide emissions and the global warming. At present, China still consumes the most coal. Under the calling for peaking carbon dioxide emissions and achieving carbon neutrality, $CO_2$ sequestration is one of the most direct and efficient ways to cultivate the technology of decarbonisation and emission reduction.

Sealed geological sites mainly include: depleted oil and gas reservoirs, deep salt water layer and coal bed which is hard to exploit, wherein the sequestration of depleted oil and gas reservoirs is widely used, and pilot tests and researches have been carried out in the field. A large amount of literature domestic and abroad also show that $CO_2$ injection into the formation can not only improve the greenhouse effect by means of sequestration, but also improve the efficiency of later recovery of oil and gas reservoirs and increase the economic benefits of the oilfield, creating certain economic value and huge ecological and environmental benefits.

During the injection of $CO_2$ into the formation, the continuous evaporation of the formation water into which dry $CO_2$ is injected will increase the $CO_2$ storage capacity, while the $CO_2$ storage capacity will decrease owing to the salt crystals left after the formation water evaporated. Therefore, there is an urgent need for a method to comprehensively evaluate the effects of formation water evaporation and salt deposition on $CO_2$ storage capacity, to facilitate timely adjustment of parameters in the subsequent $CO_2$ storage capacity scheme design, and to facilitate efficient construction in the field and effective $CO_2$ sequestration.

SUMMARY

The present disclosure aims at providing a device and method for calculating a change in $CO_2$ storage capacity before and after reservoir drying.

Technical solutions of the disclosure are as follows:

In one respect, a method for calculating a change in $CO_2$ storage capacity before and after reservoir drying is offered, which comprises of the following steps:

S1: acquire a core of the target stratum and prepare samples of formation water and gaseous $CO_2$;

S2: mix the formation water sample and the gaseous $CO_2$ sample under the target formation condition and measure the content of the saturated condensate water in the gaseous $CO_2$ sample;

S3: place the core of the target stratum in the core holder and saturate it with the formation water sample;

S4: perform a displacement experiment under the target formation condition using the gaseous $CO_2$ sample until the water saturation of the target stratum core reaches the saturation of irreducible water in the actual stratum, take out the target stratum core and record the core porosity $\phi_0$ at this time;

S5: place the target stratum core in the core holder and keep the displacement experiment using the gaseous $CO_2$ sample until all the formation water in the target stratum core has evaporated, then remove the core and record the porosity $\phi_1$ at present;

S6: calculate the drying radius of reservoir and the change of $CO_2$ storage capacity after reservoir drying.

Preferably, when the content of the saturated condensate water in the gaseous $CO_2$ sample need to be measured, firstly the mixed sample should be put into the condensing device, then the content of the condensate water and the output volume of the gaseous $CO_2$ in the device would be recorded, lastly the parameters which has been obtained could be used to calculate the content of the saturated condensate water in the gaseous $CO_2$ sample.

Preferably, the content of the saturated condensate water in the gaseous $CO_2$ sample is calculated by the following formula:

$$\omega = \frac{M_1}{G_1} \tag{1}$$

ω being the content of the saturated condensate water in the gaseous $CO_2$ sample, $M_1$ being the condensate water mass in the condensing device in g, $G_1$ being the $CO_2$ gas volume output from the condensing device in $m^3$.

Preferably, in step S6, the drying radius of the reservoir is calculated by the following formula:

$$R_0 = 0.001\sqrt{\left(\frac{Q\omega}{(\phi_1 - \phi_0)} + \pi R_1^2 h\right)\square\frac{1}{\pi h \rho_0}} \tag{2}$$

$R_0$ being the drying radius of the reservoir in m, Q being a volume of injected $CO_2$ in formation in $m^3$, ω being the content of the saturated condensate water in the gaseous $CO_2$ sample under the target formation condition in $g/m^3$, $\phi_1$ being the core porosity which is dimensionless after $CO_2$ drying under a condition of salt deposition, $\phi_0$ being the core porosity which is dimensionless under a condition of irreducible water saturation, $R_1$ being a wellbore radius in m, h being an effective thickness of the reservoir in m, $\rho_0$ being a density of the formation water sample in $kg/m^3$.

Preferably, in step S6, the change in $CO_2$ storage capacity after reservoir drying is calculated by the following formula:

$$V = 10^{-6}\left[\frac{Q\omega + \pi R_1^2 h(\phi_1 - \phi_0)}{\rho_0}\right]\square\frac{Z_1 T_1 P_2}{P_1 Z_2 T_2} \tag{3}$$

V being an increment of $CO_2$ storage capacity after reservoir drying in $m^3$, $Z_1$, which is dimensionless, being a deviation coefficient under a ground condition, $T_1$ being a temperature under the ground condition in K, $P_2$ being a pressure under the target formation condition in MPa, $P_1$ being the pressure under the ground condition in MPa, $Z_2$, which is dimensionless, being the deviation coefficient under the target formation condition, and $T_2$ being the temperature under the target formation condition in K.

As a preference, a novel displacement device is used to determine the change in $CO_2$ storage capacity before and after reservoir drying;

the novel displacement device comprises a displacement pump I, a displacement pump II, an intermediate container I, an intermediate container II, a core holder, a pressure-confining pump, a gas recovery device I, a gas recovery device II, a condensing device and a fluid sampling device;

the intermediate container I and the intermediate container II are arranged in parallel for storing the formation water sample and the gaseous $CO_2$ sample respectively; input ends of the two intermediate containers are connected to the displacement pump I, output ends of the two intermediate containers are connected to an inlet end of the core holder via pipeline I, a valve I is provided between the intermediate container I and the pipeline I, a valve II is provided between the intermediate container II and the pipeline I, and the pipeline I is successively provided with a valve III and a pressure sensor I; the output ends of the two intermediate containers are also connected to the fluid sampling device via pipeline II, and the pipeline II is successively provided with a valve IV and a pressure sensor II; the pipeline II between the valve IV and the pressure sensor II is also connected to the condensing device, and the connected pipeline is provided with a valve V, an output end of the condensing device is connected to the gas recovery device I, and the connected pipeline is provided with a gas flow meter I; the fluid sampling device is further connected to the displacement pump II, and the connected pipeline is provided with a valve VI;

the side surface of the core holder is connected to the pressure-confining pump, and a valve VII would be set on the pipelines which connect the side surface of the core holder with the pressure-confining pump; and the output end of the core holder is connected to the gas recovery device II, the pressure sensor III, the back-pressure valve and the gas flow meter are successively set on the pipelines which connect the output end of the core holder with the gas recovery device II.

Preferably, a pressure reducing valve is further provided between the intermediate container II and the valve II.

In another aspect, a device for calculating a change in $CO_2$ storage capacity before and after reservoir drying is also provided, which can be applied to the method for calculating a change in $CO_2$ storage capacity before and after reservoir drying as is mentioned above, comprising the displacement pump I, the displacement pump II, the intermediate container I, the intermediate container II, the core holder, the pressure-confining pump, the gas recovery device I, the gas recovery device II, the condensing device and the fluid sampling device;

the intermediate container I and the intermediate container II are arranged in parallel for storing the formation water sample and the gaseous $CO_2$ sample respectively; input ends of the two intermediate containers are connected to the displacement pump I, output ends of the two intermediate containers are connected to an inlet end of the core holder via pipeline I, a valve I is provided between the intermediate container I and the pipeline I, a valve II is provided between the intermediate container II and the pipeline I, and the pipeline I is successively provided with a valve III and a pressure sensor I; the output ends of the two intermediate containers are also connected to the fluid sampling device via pipeline II, and the pipeline II is successively provided with a valve IV and a pressure sensor II; the pipeline II between the valve IV and the pressure sensor II is also connected to the condensing device, and the connected pipeline is provided with a valve V, an output end of the condensing device is connected to the gas recovery device I, and the connected pipeline is provided with a gas flow meter I; the fluid sampling device is further connected to the displacement pump II, and the connected pipeline is provided with a valve VI;

the side surface of the core holder is connected to the pressure-confining pump, and a valve VII would be set on the pipelines which connect the side surface of the core holder with the pressure-confining pump; and the output end of the core holder is connected to the gas recovery device II, the pressure sensor III, the back-pressure valve and the gas flow meter are successively set on the pipelines which connect the output end of the core holder with the gas recovery device II.

Advantageous effects of the present disclosure are as follows:

Considering the influence of the salt precipitation on the $CO_2$ storage capacity during the period of the formation water evaporating, the present disclosure unprecedentedly proposes that the increase of the $CO_2$ storage capacity could be determined based on the principle of reservoir drying during the process of $CO_2$ sequestration owing to the formation water evaporating, which provides more accurate parameters in the process of $CO_2$ geological sequestration for adjusting the construction scheme and using $CO_2$ more efficiently.

In addition to calculating the change in $CO_2$ storage capacity before and after reservoir drying, the present disclosure can also be promoted to calculate the change in reservoir capacity of underground natural gas storage, underground hydrogen storage and the drying process affected by gas during the period of gas exploitation, which enjoys wide application value.

BRIEF DESCRIPTION OF DRAWINGS

In order to explain the technical solutions in the embodiments of the present disclosure or in prior art more clearly, the following contents will briefly introduce the drawings which need to be used in the embodiments or in prior art. It would be obvious that the drawings in the following description are only embodiments of the present disclosure, and it is possible for a normal technician in this field to gain other drawings according to the following drawings without any creative effort.

Figure 1:
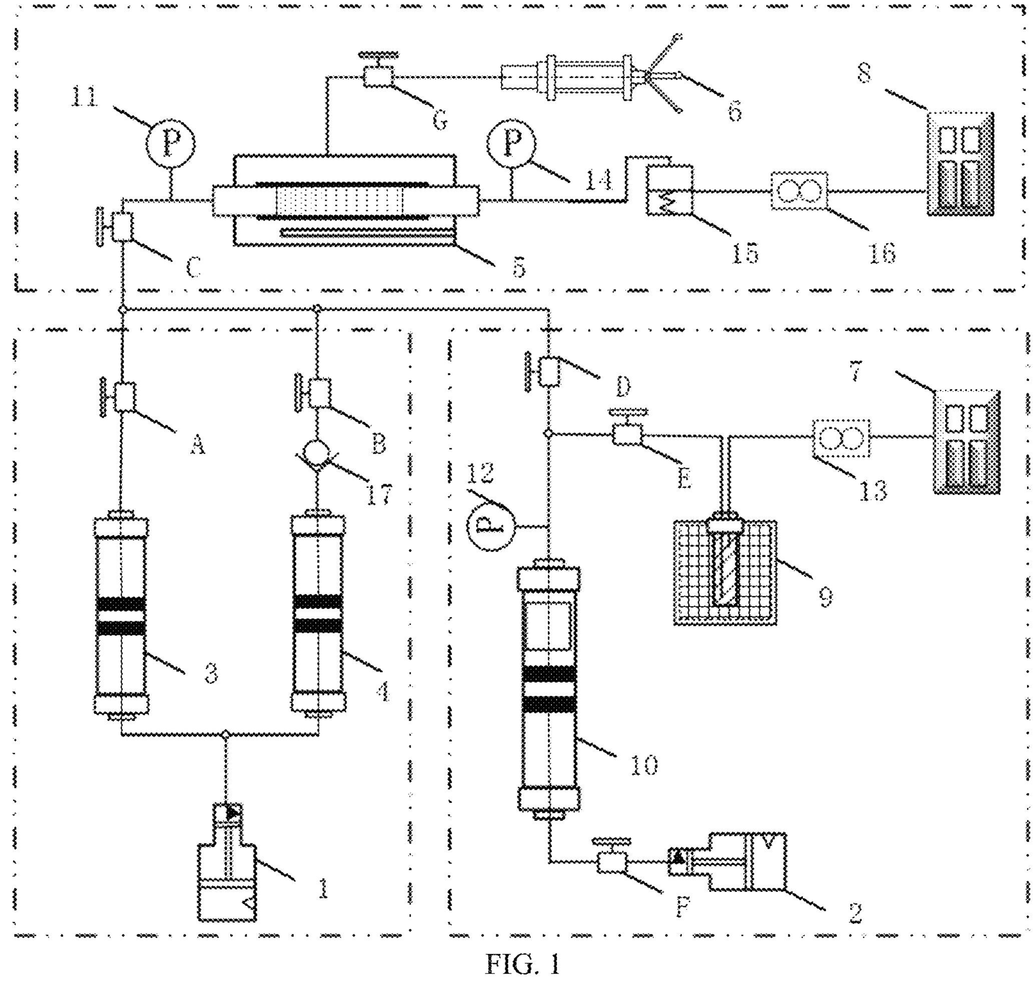
FIG. 1 is a schematic structural diagram of a novel displacement device according to a specific embodiment.
Figure 2:
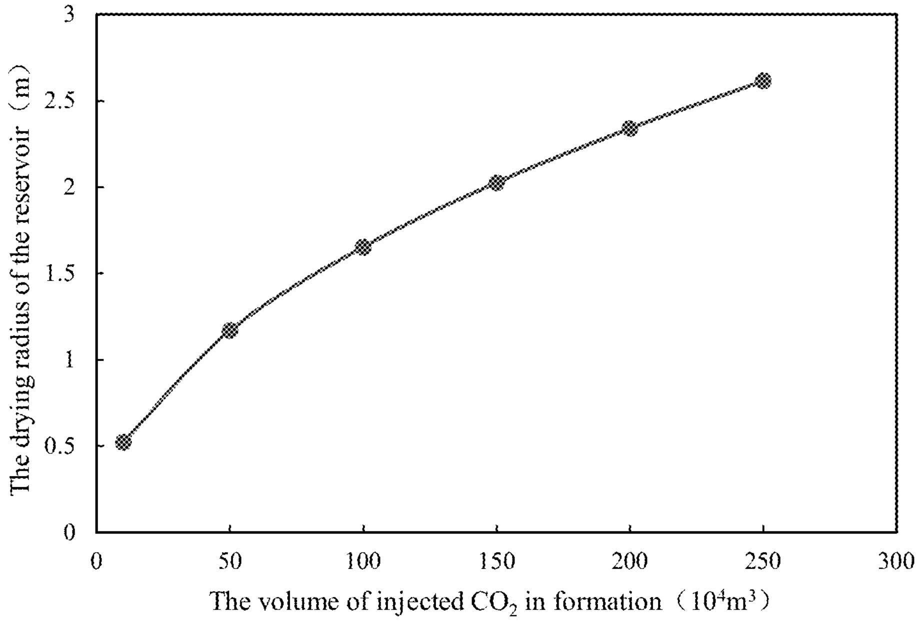
FIG. 2 is a schematic diagram of a calculated result of a drying radius for a reservoir according to a specific embodiment.

REFERENCE NUMERALS IN THE FIGs.

1—displacement pump I, 2—displacement pump II, 3—intermediate container I, 4—intermediate vessel II, 5—core holder, 6—pressure-confining pump 7—gas recovery device I, 8—gas recovery device II, 9—condensing device, 10—fluid sampling device, 11—pressure sensor I, 12—pressure sensor II, 13—gas flow meter I, 14—pressure sensor III, 15—back pressure valve, 16—gas flow meter II, 17—pressure reducing valve, A—valve I, B—valve II, C—valve III, D—valve IV, E—valve V, F—valve VI, G—valve VII.

DETAILED DESCRIPTION OF THE EMBODIMENTS

The present disclosure is further illustrated in combination with the figures and the embodiments. It should be noted that with no conflict occurring, the embodiments and technical features in the present disclosure can be combined with each other. It should be noted that, unless indicated otherwise, all technical and scientific terms used herein have the same meaning as commonly understood by a normal technician in the field to which the present disclosure belongs. The use of "including" or "comprising" and the like in the context of the present disclosure means that the presence of an element or item preceding the word covers the presence of the element or item listed after the word and its equivalents, but does not exclude other elements or items.

The present disclosure provides a method for calculating a change in $CO_2$ storage capacity before and after reservoir drying, which comprises the following steps:

S1: acquire a core of the target stratum and prepare samples of formation water and gaseous $CO_2$;

S2: mix the formation water sample and the gaseous $CO_2$ sample under the target formation condition and measure the content of the saturated condensate water in the gaseous $CO_2$ sample;

In a specific embodiment, when the content of the saturated condensate water in the gaseous $CO_2$ sample is measured, a mixed sample is firstly introduced into a condensing device, then a condensate water mass in the condensing device and a $CO_2$ gas volume output from the condensing device are recorded, and finally the content of the saturated condensate water in the gaseous $CO_2$ sample is calculated according to obtained parameters; and the content of the saturated condensate water in the gaseous $CO_2$ sample is calculated by the following formula:

$$\omega = \frac{M_1}{G_1} \tag{1}$$

$\omega$ being the content of the saturated condensate water in the gaseous $CO_2$ sample under the target formation condition in $g/m^3$, $M_1$ being the condensate water mass in the condensing device in g, $G_1$ being the $CO_2$ gas volume output from the condensing device in $m^3$.

S3: place the core of the target stratum in the core holder and saturate it with the formation water sample.

S4: perform a displacement experiment under the target formation condition using the gaseous $CO_2$ sample until the water saturation of the target stratum core reaches the saturation of irreducible water in the actual stratum, take out the target stratum core and record a core porosity $\phi_0$ at this time.

S5: place the target stratum core in the core holder and keep the displacement experiment using the gaseous $CO_2$ sample until all the formation water in the target stratum core has evaporated, then remove the core and record the porosity $\phi_1$ at present.

S6: calculate the drying radius of reservoir and the change of $CO_2$ storage capacity after reservoir drying.

In a specific embodiment, the drying radius of the reservoir is calculated by the following formula:

$$R_0 = 0.001\sqrt{\left(\frac{Q\omega}{(\phi_1 - \phi_0)} + \pi R_1^2 h\right)\square\frac{1}{\pi h \rho_0}} \tag{2}$$

$R_0$ being the drying radius of the reservoir in m, Q being a volume of injected $CO_2$ in formation in $m^3$, $\omega$ being the content of the saturated condensate water in the gaseous $CO_2$ sample under the target formation condition in $g/m^3$, $\phi_1$ being the core porosity which is dimensionless after $CO_2$ drying under a condition of salt deposition, $\phi_0$ being the core porosity which is dimensionless under a condition of the saturation of irreducible water, $R_1$ being a wellbore radius in m, h being an effective thickness of the reservoir in m, $\rho_0$ being a density of the formation water sample in $kg/m^3$.

The change in $CO_2$ storage capacity after reservoir drying is calculated by the following formula:

$$V = 10^{-6}\left[\frac{Q\omega + \pi R_1^2 h(\phi_1 - \phi_0)}{\rho_0}\right]\square\frac{Z_1 T_1 P_2}{P_1 Z_2 T_2} \tag{3}$$

V being an increment of $CO_2$ storage capacity after reservoir drying in $m^3$, $Z_1$, which is dimensionless, being a deviation coefficient under a ground condition, $T_1$ being a temperature under the ground condition in K, $P_2$ being a pressure under the target formation condition in MPa, $P_1$ being a pressure under the ground condition in MPa, $Z_2$, which is dimensionless, being a deviation coefficient under the target formation condition, and $T_2$ being a temperature under the target formation condition in K.

In a specific embodiment, a novel displacement device is used to determine the change in $CO_2$ storage capacity before and after reservoir drying; the novel displacement device comprises a displacement pump I 1, a displacement pump II 2, an intermediate container I 3, an intermediate container II 4, a core holder 5, a pressure-confining pump 6, a gas recovery device I 7, a gas recovery device II 8, a condensing device 9 and a fluid sampling device 10;

the intermediate container I 3 and the intermediate container II 4 are arranged in parallel for storing the formation water sample and the gaseous $CO_2$ sample respectively; input ends of the two intermediate containers are connected to the displacement pump I 1, output ends of the two intermediate containers are connected to an inlet end of the core holder 5 via pipeline I, a valve I A is provided between the intermediate container I 3 and the pipeline I, a valve II B is provided between the intermediate container II 4 and the pipeline I, and the pipeline I is successively provided with a valve III C and a pressure sensor I 11; the output ends of the two intermediate containers are also connected to the fluid sampling device 10 via pipeline II, and the pipeline II is successively provided with a valve IV D and a pressure sensor II 12; the pipeline II between the valve IV D and the pressure sensor II 12 is also connected to the condensing device 9, and the connected pipeline is provided with a valve V E, an output end of the condensing device 9 is connected to the gas recovery device I 7, and the connected pipeline is provided with a gas flow meter I 13; the fluid sampling device 10 is further connected to the displacement pump II 2, and the connected pipeline is provided with a valve VI F;

a side surface of the core holder 5 is connected to the pressure-confining pump 6, and the connected pipeline is provided with a valve VII G; and an output end of the core holder 5 is connected to the gas recovery device II 8, and the connected pipeline is successively provided with a pressure sensor III 14, a back pressure valve 15 and a gas flow meter II 16.

Optionally, a pressure reducing valve 17 is further provided between the intermediate container II 4 and the valve II 17.

In the above-mentioned embodiment, the device mentioned in the step S2, which is required to measure the content of saturated condensate water in the gaseous $CO_2$ sample, can be assembled with the devices needed for the subsequent displacement experiment, that said, only one device is enough for the experiment, which makes operation easier. It should be noted that the content of the saturated condensate water in the gaseous $CO_2$ sample can also be measured separately, then existing techniques in this field can be adopted to perform the displacement experiment as well.

Taking the W gas field as an example, by means of the method for calculating a change in $CO_2$ storage capacity before and after the reservoir drying, the change in $CO_2$ storage capacity before and after the reservoir drying of the target reservoir can be fixed, which comprises the following steps:

(1) acquire a target stratum core and prepare a formation water sample and a gaseous $CO_2$ sample, in this example, the base parameters of the target stratum core being shown in Table 1:

TABLE 1

Basic parameters of the target stratum core

| Serial number | Core number | Dry weight (g) | Length (mm) | Diameter (mm) | Porosity | Permeability (mD) |
|---|---|---|---|---|---|---|
| 1 | 242-4 | 53.1102 | 50.94 | 24.50 | 0.1621 | 8.496 |

(2) place the formation water sample into the intermediate container I, place the gaseous $CO_2$ sample into the middle container II, and place the target stratum core into the core holder;

(3) measure the content of the saturated condensate water in $CO_2$ under the target formation condition;

open valve I A, valve II B and valve IV D, inject the excessive formation water sample and gaseous $CO_2$ sample into the fluid sampling device 10, set the temperature and pressure of the fluid sampling device 10 under the target formation condition (128° C., 30 MPa), stir for 2 hours, face the part where the gaseous $CO_2$ is located upwards, open the valve V E to allow the gas to pass through the condensing device 9 at the speed of 50 mL/min, record the content of the condensate water in the condensing device 9 as 8.9 g, the volume of $CO_2$ passing through the gas flow meter I 13 as 1.33 m$^3$, wherein the content of the saturated condensate water of $CO_2$ under the condition of formation temperature and pressure is 6.7 g/m$^3$ as calculated by formula (1);

(4) measure the effects of formation water evaporation on physical properties of reservoir considering salt deposition;

open valve I A, valve III C, and back pressure valve 15, and use the formation water to saturate the core in the intermediate container I; close valve I A, open valve II B, use the gaseous $CO_2$ sample in the intermediate container II to displace the core at a rate of 5 mL/min until the water saturation reaches the saturation of the irreducible water in the actual formation, and take out the core to measure the porosity $\phi_0$ thereof under the irreducible water saturation condition to be 0.0931; then use the gaseous $CO_2$ sample to continuously displace the core for 4 hours until all the formation water in the core evaporated, and after taking out the core, measure the core porosity $\phi_0$ after $CO_2$ drying under the condition of salt deposition to be 0.1476; and (5) calculate the drying radius of reservoir and record the change of $CO_2$ storage capacity after reservoir drying.

Figure 3:
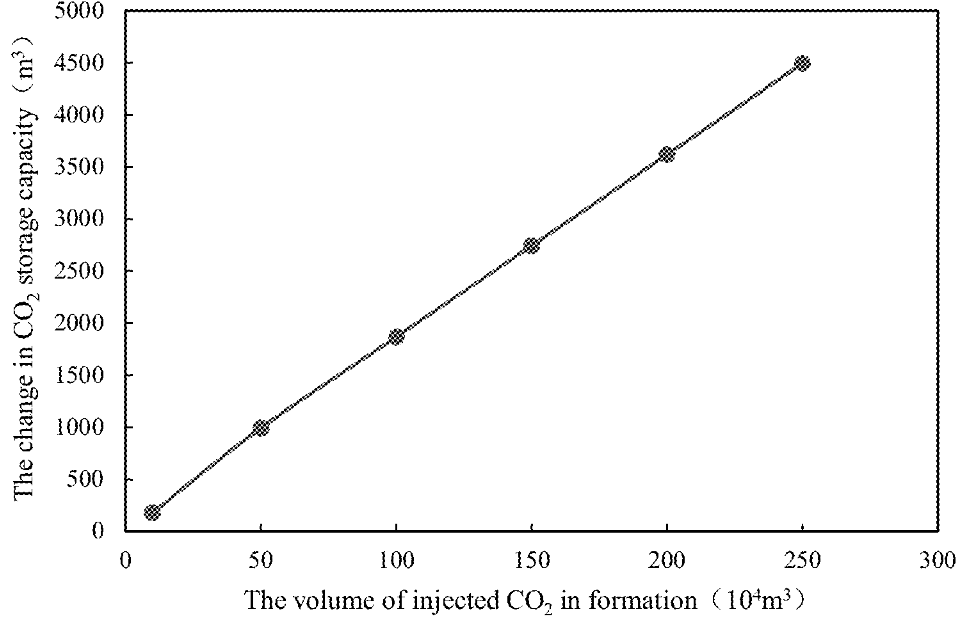
FIG. 3 is a schematic diagram of the calculated result of a change in $CO_2$ storage capacity after drying the reservoir according to a specific embodiment.

In this embodiment, the wellbore radius of the well is 0.1 m, an effective thickness of the reservoir is 13.5 m, a ground surface temperature is 20° C., a ground surface pressure is 0.1 MPa, the deviation coefficient under the ground condition is 0.9964, the deviation coefficient under the formation condition is 0.7055, and a formation water density is 1.18 g/cm$^3$. The drying radius of the reservoir and the change results of the $CO_2$ storage capacity after the reservoir drying obtained by the calculation of formulae (2) and (3) are shown in Table 2 and FIGS. 3 and 4.

TABLE 2

Drying radius of reservoir and change results of $CO_2$ storage capacity storage capacity after reservoir drying

| Serial number | $CO_2$ injection amount ($10^4$ m$^3$) | Drying radius (m) | Increment of storage capacity (m$^3$) |
|---|---|---|---|
| 1 | 10 | 0.523 | 180.964 |
| 2 | 50 | 1.169 | 993.168 |
| 3 | 100 | 1.654 | 1868.898 |
| 4 | 150 | 2.026 | 2744.627 |
| 5 | 200 | 2.339 | 3620.357 |
| 6 | 250 | 2.615 | 4496.087 |

To sum up, the present disclosure can calculate the $CO_2$ storage capacity more accurately with taking the effect of the formation water evaporating and salt deposition on the $CO_2$ storage capacity into account. The present disclosure makes a remarkable advance compared with existing techniques.

While what is presented above is just an embodiment that is preferable to others, it never limits the present disclosure in any shape or form. A preferred embodiment claimed above does not limit the present disclosure though. Any technician skilled in this field could utilize the technology claimed above to make some slight changes or modifications within the present disclosure, which could also be considered as an equivalent embodiment. Whatever does not break away the content of the present disclosure above, with simple amendments, equivalent changes or modifications, still lies in the ambit of this present disclosure.

What is claimed is:

1. A method for calculating a change in $CO_2$ storage capacity before and after reservoir drying,

S1: acquire a core of the target stratum and prepare samples of formation water and gaseous $CO_2$;

S2: mix the formation water sample and the gaseous $CO_2$ sample under the target formation condition and measure the content of the saturated condensate water in the gaseous $CO_2$ sample;

S3: place the core of the target stratum in the core holder and saturate it with the formation water sample;

S4: perform a displacement experiment under the target formation condition using the gaseous $CO_2$ sample until the water saturation of the target stratum core reaches the saturation of irreducible water in the actual stratum, take out the target stratum core and record a core porosity do at this time;

S5: place the target stratum core in the core holder and keep the displacement experiment using the gaseous $CO_2$ sample until all the formation water in the target stratum core has evaporated, then remove the core and record the porosity $\phi$1 at present; and

S6: calculate the drying radius of reservoir and the change of $CO_2$ storage capacity after reservoir drying;

wherein in step S2, when the content of the saturated condensate water of the gaseous $CO_2$ sample is measured, a mixed sample is firstly introduced into a condensing device, then a condensate water mass in the condensing device and a $CO_2$ gas volume output from the condensing device are recorded, and finally the content of the saturated condensate water of the gaseous $CO_2$ sample is calculated according to obtained parameters.

2. The method for calculating a change in $CO_2$ storage capacity before and after reservoir drying according to claim 1, wherein the content of the saturated condensate water of the gaseous $CO_2$ sample is calculated by the following formula:

$$\omega = \frac{M_1}{G_1} \tag{1}$$

$\omega$ being the content of the saturated condensate water of the gaseous $CO_2$ sample under the target formation condition in g/m$^3$, $M_1$ being the condensate water mass in the condensing device in g, $G_1$ being the $CO_2$ gas volume output from the condensing device in m$^3$.

3. The method for calculating a change in $CO_2$ storage capacity before and after reservoir drying according to claim 1, wherein in step S6, the drying radius of the reservoir is calculated by the following formula:

$$R_0 = 0.001\sqrt{\left(\frac{Q\omega}{(\phi_1 - \phi_0)} + \pi R_1^2 h\right)\cdot\frac{1}{\pi h \rho_0}} \tag{2}$$

$R_0$ being the drying radius of the reservoir in m, Q being a volume of injected $CO_2$ in formation in m$^3$, $\omega$ being the content of the saturated condensate water of the gaseous $CO_2$ sample under the target formation condition in g/m$^3$, $\phi_1$ being the core porosity which is dimensionless after $CO_2$ drying under a condition of salt deposition, $\phi_0$ being the core porosity which is dimensionless under a condition of saturation of irreducible water, $R_1$ being a wellbore radius in m, h being an effective thickness of the reservoir in m, $\rho_0$ being a density of the formation water sample in kg/m$^3$.

4. The method for calculating a change in $CO_2$ storage capacity before and after reservoir drying according to claim 3, wherein in step S6, the change in $CO_2$ storage capacity after reservoir drying is calculated by the following formula:

$$V = 10^{-6}\left[\frac{Q\omega + \pi R_1^2 h(\phi_1 - \phi_0)}{\rho_0}\right]\cdot\frac{Z_1 T_1 P_2}{P_1 Z_2 T_2} \tag{3}$$

V being an increment of $CO_2$ storage capacity after reservoir drying in m$^3$, $Z_1$, which is dimensionless, being a deviation coefficient under a ground condition, $T_1$ being a temperature under the ground condition in K, $P_2$ being a pressure under the target formation condition in MPa, $P_1$ being a pressure under the ground condition in MPa, $Z_2$, which is dimensionless, being a deviation coefficient under the target formation condition, and $T_2$ being a temperature under the target formation condition in K.

5. The method for calculating a change in $CO_2$ storage capacity before and after reservoir drying according to claim 1, wherein a novel displacement device is used to determine the change in $CO_2$ storage capacity before and after reservoir drying;

the novel displacement device comprises a displacement pump I, a displacement pump II, an intermediate container I, an intermediate container II, a core holder, a pressure-confining pump, a gas recovery device I, a gas recovery device II, a condensing device and a fluid sampling device;

the intermediate container I and the intermediate container II are arranged in parallel for storing the formation water sample and the gaseous $CO_2$ sample respectively; input ends of the two intermediate containers are connected to the displacement pump I, output ends of the two intermediate containers are connected to an inlet end of the core holder via pipeline I, a valve I is provided between the intermediate container I and the pipeline I, a valve II is provided between the intermediate container II and the pipeline I, and the pipeline I is successively provided with a valve III and a pressure sensor I; the output ends of the two intermediate containers are also connected to the fluid sampling device via pipeline II, and the pipeline II is successively provided with a valve IV and a pressure sensor II; the pipeline II between the valve IV and the pressure sensor II is also connected to the condensing device, and the connected pipeline is provided with a valve V, an output end of the condensing device is connected to the gas recovery device I, and the connected pipeline is provided with a gas flow meter I; the fluid sampling device is further connected to the displacement pump II, and the connected pipeline is provided with a valve VI;

a side surface of the core holder is connected to the pressure-confining pump, and the connected pipeline is provided with a valve VII; and an output end of the core holder is connected to the gas recovery device II, and the connected pipeline is successively provided with a pressure sensor III, a back pressure valve and a gas flow meter II.

6. The method for calculating a change in $CO_2$ storage capacity before and after reservoir drying according to claim 5, wherein a pressure reducing valve is further provided between the intermediate container II and the valve II.

7. A device for calculating a change in $CO_2$ storage capacity before and after reservoir drying, used for the method for calculating a change in $CO_2$ storage capacity before and after reservoir drying according to claim 1, comprising a displacement pump I, a displacement pump II, an intermediate container I, an intermediate container II, a core holder, a pressure-confining pump, a gas recovery device I, a gas recovery device II, a condensing device and a fluid sampling device;

the intermediate container I and the intermediate container II are arranged in parallel for storing the formation water sample and the gaseous $CO_2$ sample respectively; input ends of the two intermediate containers are connected to the displacement pump I, output ends of the two intermediate containers are connected to an inlet end of the core holder via pipeline I, a valve I is provided between the intermediate container I and the pipeline I, a valve II is provided between the intermediate container II and the pipeline I, and the pipeline I is successively provided with a valve III and a pressure sensor I; the output ends of the two intermediate containers are also connected to the fluid sampling device via pipeline II, and the pipeline II is successively provided with a valve IV and a pressure sensor II; the pipeline II between the valve IV and the pressure sensor II is also connected to the condensing device, and the connected pipeline is provided with a valve V, an output end of the condensing device is connected to the gas recovery device I, and the connected pipeline is provided with a gas flow meter I; the fluid sampling device is further connected to the displacement pump II, and the connected pipeline is provided with a valve VI;

a side surface of the core holder is connected to the pressure-confining pump, and the connected pipeline is provided with a valve VII; and an output end of the core holder is connected to the gas recovery device II, and the connected pipeline is successively provided with a pressure sensor III, a back pressure valve and a gas flow meter II.

8. The device for calculating a change in $CO_2$ storage capacity before and after reservoir drying according to claim 7, wherein a pressure reducing valve is provided between the intermediate container II and the valve II.

* * * * *